United States Patent [19]
Gabard

[11] Patent Number: 4,693,723
[45] Date of Patent: Sep. 15, 1987

[54] SHOULDER PROSTHESIS

[75] Inventor: Jean-Jacques Gabard, Maule, France

[73] Assignee: Commissariat a l'Energie Atomique, Paris, France

[21] Appl. No.: 709,606

[22] Filed: Mar. 7, 1985

Related U.S. Application Data

[63] Continuation-in-part of Ser. No. 604,936, Apr. 27, 1984, abandoned.

[30] Foreign Application Priority Data

May 2, 1983 [FR] France ................... 83 07251

[51] Int. Cl.$^4$ .................................. A61F 2/40
[52] U.S. Cl. ...................................... 623/19
[58] Field of Search ........................ 623/18, 19, 20, 21, 623/22, 23; 128/92 C, 92 CA

[56] References Cited

U.S. PATENT DOCUMENTS

| | | | |
|---|---|---|---|
| 3,842,442 | 10/1974 | Kolbel | 623/19 |
| 3,916,451 | 11/1975 | Buechel et al. | 623/19 |
| 3,978,528 | 9/1976 | Grep | 623/19 |

Primary Examiner—Richard J. Apley
Assistant Examiner—David J. Isabella

[57] ABSTRACT

A prosthesis for mechanical suspension on a human shoulder blade utilizing a swivel joint system formed by a sphere adapted to be fixed to the shoulder blade by a rod integral with an implant anchored in the shoulder blade socket, as well as a humeral cupula articulated to the sphere and adapted to be fixed to the humerus by a diaphyseal projection supporting the cupula and implanted in the humerus, the cupula having a hollow inner hemispherical surface and an open side terminating in surface edges, the axis of the diaphyseal projection passing approximately through the center of the sphere and forming an angle of about 10° with a plane coextensive with the surface edges of the cupula, the sphere being forcefitted directly into the cupula which surrounds the sphere over half the circumference thereof and thereby retains the same, the axis of the rod for fixing the sphere to the shoulder blade socket being eccentrically located with respect to the sphere; and the outer surface of the humeral cupula being hemispherical, concentric with the hollow inner hemispherical surface thereof, and is of a diameter close to that of a normal anatomical humeral head.

8 Claims, 9 Drawing Figures

SHOULDER PROSTHESIS

This application is a continuation-in-part of U.S. Ser. No. 604,936 filed Apr. 27, 1984 and now abandoned.

The present invention relates to a shoulder prosthesis and more particularly to a prosthesis which is free from dislocation risks in all positions of the arm, even in the case of marked weakness or significant degeneration of the muscular tissues and tendons normally ensuring the suspension of the shoulder on the shoulder blade.

BACKGROUND OF THE INVENTION

To make the object of the invention more readily comprehensible, firstly the anatomical structure of a normal human shoulder will be described with reference to FIG. 1.

FIG. 1 shows a normal human shoulder which, in per se known manner, comprises a shoulder blade 11 and a humerus, whereof it is possible to see the upper part 16 and the humeral head 22. The substantially spherical humeral head 22 is in contact with the socket 2 of shoulder blade 11, which is a cartilaginous cavity against which slides and rolls said humeral head 22. The special feature of such a joint is that humerus 16 is held in place against shoulder blade 11 solely by passive suspension with the aid of ligaments 23a,b and active suspension with the aid of periarticular muscles connecting humerus 16 and shoulder blade 11.

In the case of acute or chronic degenerative lesions of the shoulder or fractures of the head, the humeral neck or the scapular socket, it is sometimes necessary to replace the affected or fractured parts by prosthetic implants on the humerus and shoulder blade.

Different prosthetic replacements of the shoulder have already been proposed.

The first, more particularly proposed following fractures to the humeral head prevent any assistance by osteosynthesis (screws, plates, pins), consist of a humeral prosthetic member, either sealed or not sealed with cement in the diaphyseal shaft of the humerus following the exeresis of the fractured fragments of the humeral head.

Other prostheses were then proposed and were directed towards a complete prosthetic implant, i.e. the replacement of the humeral head associated with the replacement, after exeresis, of the glenoid articular cartilage (shoulder blade) in contact with said prosthetic head.

These different solutions suffer from numerous disadvantages.

Thus, even though the positioning of the glenoid member causes no major problems, the orientation in rotation of the humeral member is difficult, due to the operating conditions and the lack of a reference point for the surgeon to establish proper spacial orientation; following the resection of the humeral head.

Moreover, the clinical results are often impaired by the fact that the condition of the muscles is often not very good prior to the operation, e.g. in elderly patients, whose musculature is not well developed in the case of a fracture, or a shoulder which has been locked for several years in the case of degenerative ailments. Furthermore, the muscular tissue is also impaired by the actual operation, which makes it necessary to cut through certain muscles in order to obtain access to the joint.

Finally, and more particularly, when there is no mechanical connection between the individual prosthetic members, either a swinging shoulder, or a very significant reduction in movements due to the reduction or absence of the synergy of the motor muscles of said prosthesized joint results.

Thus, in a normal shoulder, the stability of the humeral head is ensured, as has been seen relative to FIG. 1, by ligaments, the articular capsule and the muscles of the rotary cuff.

The ailment or disease in question, which may or may not be traumatic, leads to a deterioration of certain muscles and this is further impaired by surgery and there is a risk of injury to the ligaments and the articular capsule, through which it is necessary to pass and then repair.

It is for this reason that a second type of shoulder prostheses, illustrated e.g. by U.S. Pat. Nos. 3,978,528 and 4,206,517 have been proposed, in which all efforts have been directed at producing an artificial swivel jointed shoulder unlinked with the normal shoulder, while making no effort to restore the anatomical shoulder. In such prostheses a spherical head fixed to the shoulder blade swivels in a spherical hollow recess or cupula fixed to the humerus and takes the place of the old head, using a diaphyseal projection cemented into the humerus axis.

The designers of such prostheses correctly thought that a swivel joint is mechanically more satisfactory than a rolling contact and were clearly inspired, as can be gathered from U.S. Pat. No. 4,206,517, by the hip joint (cf. FIGS. 13, 14 and 15). However, on the one hand the operating conditions of the shoulder (generally in traction) are very different from those of the hip (generally in compression) and, on the other hand, the possibilities of dislocations of the prostheses described in U.S. Pat. Nos. 3,978,528 and 4,206,517 are very real, if the system of ligaments and support muscles is in any way inadequate.

Thus, in the two aforementioned patents, the diaphyseal projection forms an angle of approximately 60° with the free surface of the cupula, which makes it necessary to connect said projection in the vicinity of the apex of the hemisphere constituting the cupula. It is also necessary to provide an intermediate mechanical system (catching plastic washer 38 in U.S. Pat. No. 3,978,528 and the association of a rigid box 14 and an elastic washer 15 in U.S. Pat. No. 4,206,517) for locking the sphere in its recess and making the cupula retentive, particularly when the arm is lowered. In other words, the risk of shoulder dislocation is only obviated through the presence of a necessarily fragile and degradable, intermediate system.

Finally, as a result of the fact that in these constructions the axis of the diaphyseal projection—or the humerus—does not pass through the centre of the swivelling sphere produces a complementary torque of the traction force of the arm with respect to the centre of the swivel joint, which makes such designs even more delicate.

All the aforementioned disadvantages have meant that hitherto no such swivel jointed shoulder prostheses have been fitted and they have remained at the planning stage.

The object of the total prosthesis according to the invention is to obviate the aforementioned disadvantages and its special construction, mechanically suspended on the shoulder blade, makes it possible to obviate any risk of dislocations, even in the case of a serious failure of the conventional support muscle and/or ligament systems of the normal shoulder.

SUMMARY OF THE INVENTION

The invention relates to a human shoulder mechanically suspended on the shoulder blade and which is free from any dislocation risk in all arm positions, of the type comprising a swivel joint system formed by a sphere fixed to the shoulder blade via a fixing rod integral with an implant anchored in the socket, as well as a humeral cupula articulated to the sphere and fixed to the humerus by a diaphyseal projection supporting the cupula and implanted in the humerus, characterized in that the axis of the diaphyseal projection passes approximately through the center of the sphere and its angle with a plane formed by the surface edges of the cupula is close to 10°; the sphere is forcefitted directly into the cupula, which is retentive with respect to said sphere, which it surrounds over half of the sphere; the axis of the rod for fixing the sphere to the shoulder blade socket is eccentrically located with respect to the sphere; the outer surface of the humeral cupula is spherical, concentric with the hollow inner sphere of the cupula and has a diameter close to that of a normal anatomical humeral head.

The present invention also relates to the following preferred arrangements, considered in isolation or in combination:

(a) the socket L-shaped plate is extended at the bottom by a short leg covering the axillary edge of the shoulder blade;

(b) the socket L-shaped plate has holes for fitting screws directed towards the coracoid base, towards the acromion base and towards the axillary edge of the shoulder blade;

(c) the short leg of the socket L-shaped plate has holes for fitting a pin passing through the axillary edge;

(d) the socket L-shaped plate; carries on its inner face a retaining part, whose head is wider than its base and which is embedded in a fixing cement.

BRIEF DESCRIPTION OF THE DRAWINGS

These characteristics and a certain number of further characteristics, together with the way in which the prosthesis according to the invention is fitted, will be described in greater detail hereinafter with reference to the attached drawings, which show.

Figure 1:
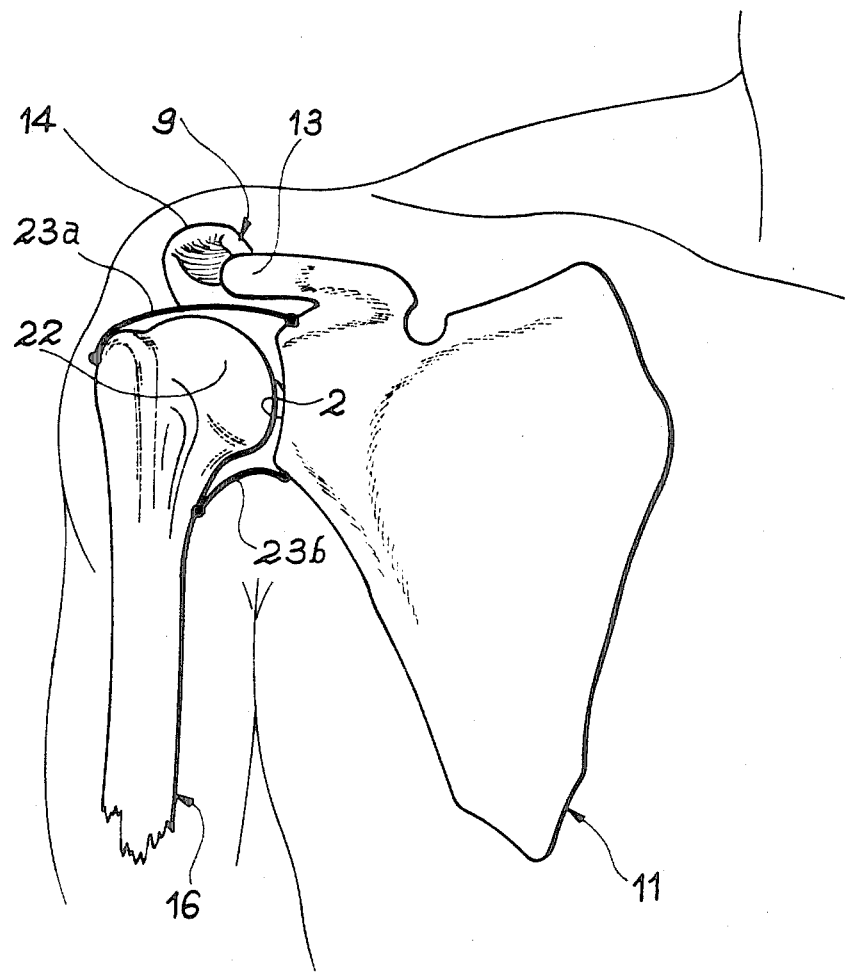
FIG. 1 an anatomical view of a human shoulder.

In all the aforementioned drawings, it is important for the purpose of understanding the invention, that gravity is always directed towards the bottom of the drawings, to be studied in conjunction with the following description.

DESCRIPTION OF THE PREFERRED EMBODIMENTS

On referring to these drawings, it can be seen that the total prosthesis of the invention comprises a combination of a socket part, formed by a L-shaped plate member 1 covering the socket 2 of the shoulder blade 11, carrying an arm 3 terminated at its end by a sphere or ball 4, with a humeral part formed by a hemispherical cupula 5 exceeding the diameter of ball 4 and carrying a projection 6 for implantation in the diaphyseal shaft of the humerus 16.

Figure 2:
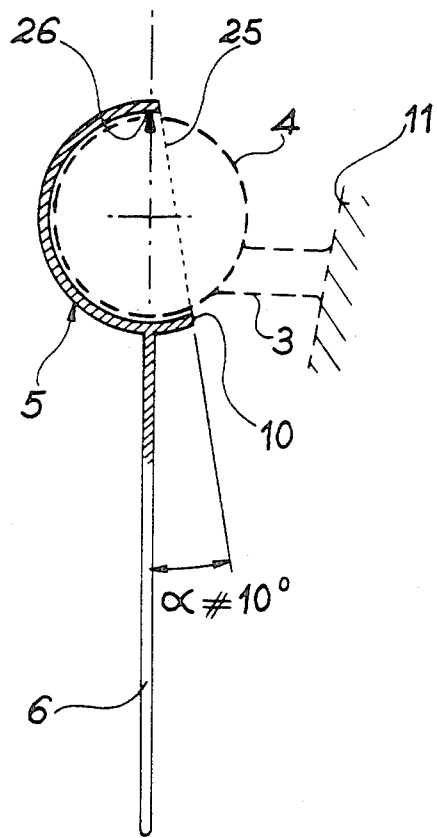
FIG. 2 a basic diagram of the prosthesis according to the invention, showing how it is mechanically suspended in a non-disconnectable manner on the shoulder blade, even when there are no support muscles.

FIG. 2 shows a basic sectional diagram of the prosthesis, where it is possible to see the diaphyseal projection 6 and the hemispherical cupula 5 which it supports, cupula 5 serving to house a sphere 4 fixed by the fixing rod 3 to shoulder blade 11. According to the invention, the diaphyseal projection 6 is connected to cupula 5 in the vicinity of the outer surface or opening edge 10 of said cupula and it forms an angle $\alpha$ of close to 10° with a plane 25 formed by the substantially flat surface edges of said cupula. Thus, and this is one of the main characteristics of the invention, the assembly formed by the diaphyseal projection and cupula 5 is attached to and suspended within sphere 4, the suspension point 26 being positioned in the upper part of cupula 5 in the vicinity of its opening edge 10. In the position shown in FIG. 2, which is the normal arm position hanging along the body, it can be seen that any complimentary traction exerted on the humerus in which rod 6 is sealed will reinforce the mechanical stability of the swivel joint, which is therefore absolutely non-disconnectable. If a comparison is desired to illustrate what has been stated hereinbefore, it can be said that the shoulder prosthesis according to the invention is attached by gravity to sphere 4, in the same way as a garment placed on the spherical head of a coat peg. This explains the novel special feature of the shoulder prosthesis according to the invention, which is that it does not have to be held in place by muscles or ligaments in order to function in a non-detachable manner.

Figure 3A:
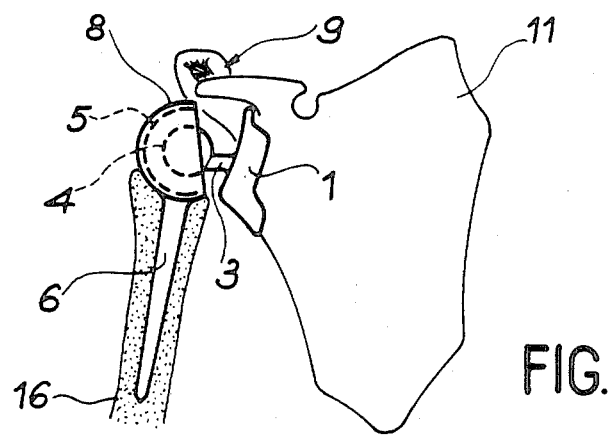
FIGS. 3a, 3b and 3c provide a better understanding of the permanence of the non-disconnectable state of said prosthesis in three different arm positions.
Figure 3B:
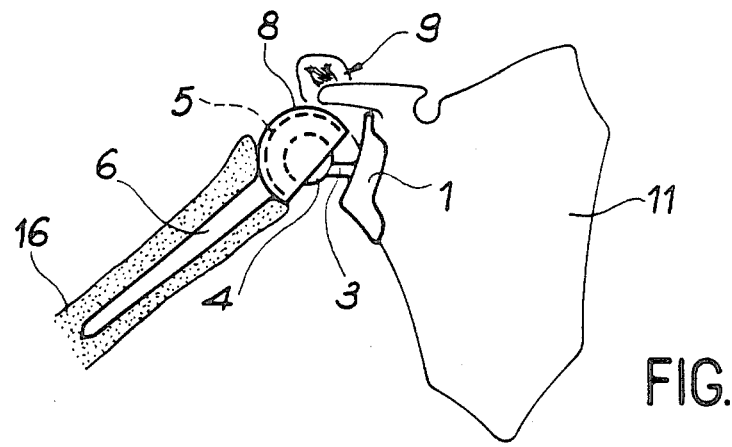
Figure 3C:
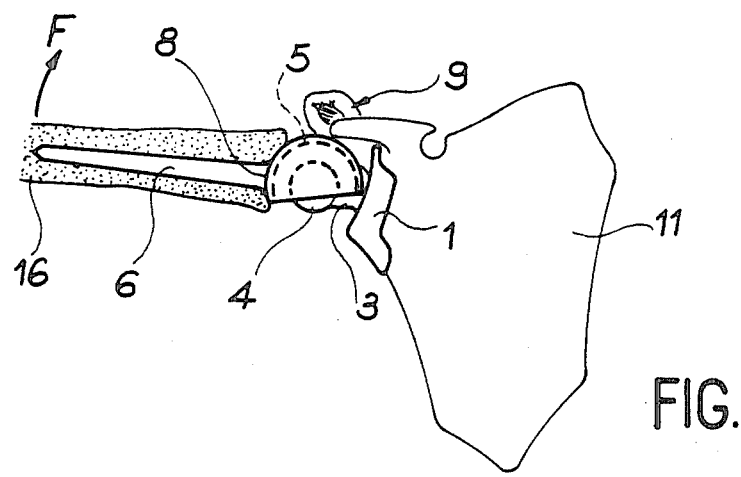
Figure 5:
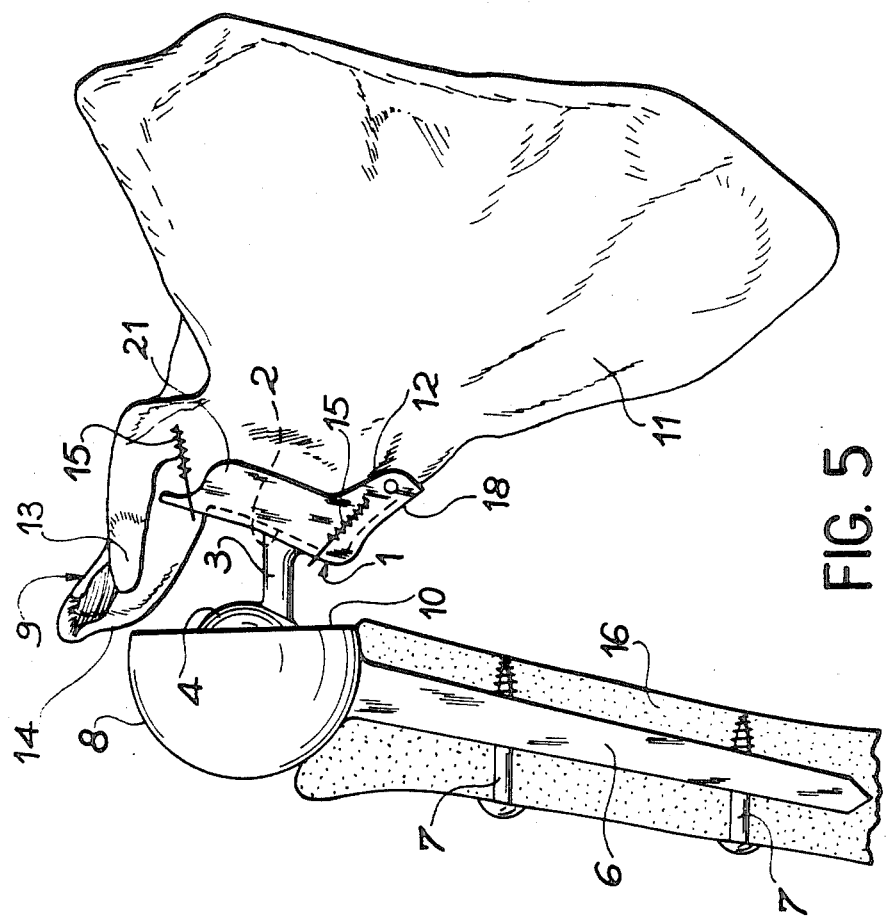
FIG. 5 a part sectional elevation of the fitted prosthesis of FIG. 2.
Figure 4:
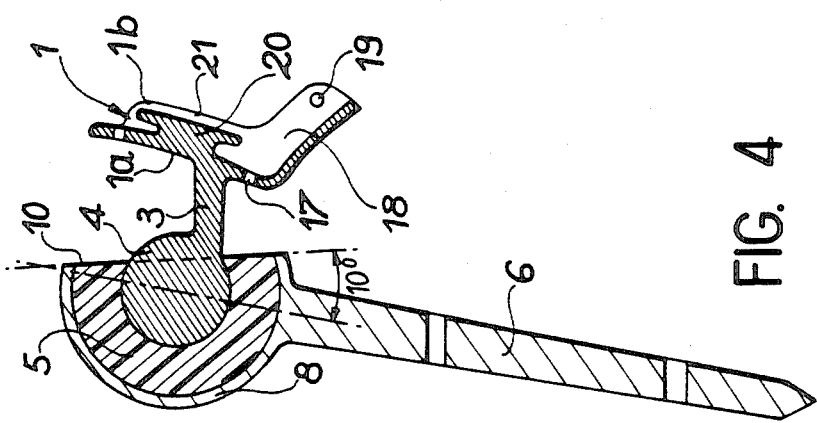
FIG. 4 a longitudinal sectional view of a preferred embodiment of the invention.
Figure 6:
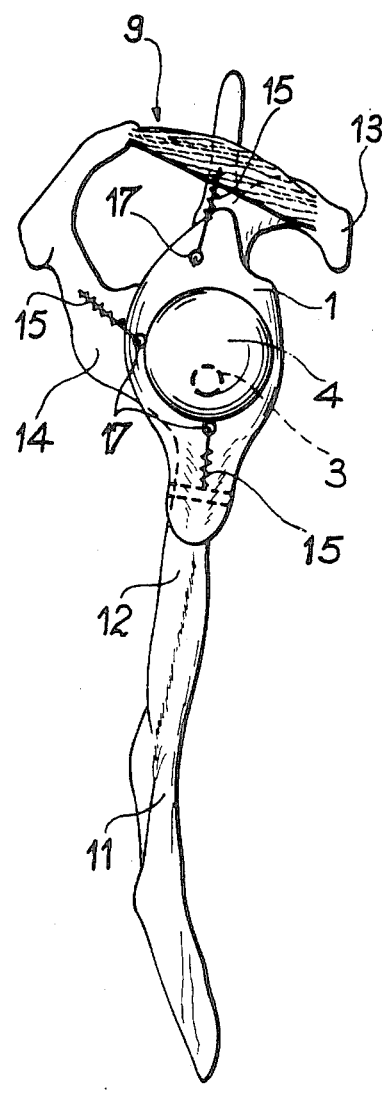
FIG. 6 an end view of the socket part with representation of the shoulder blade.
Figure 7:
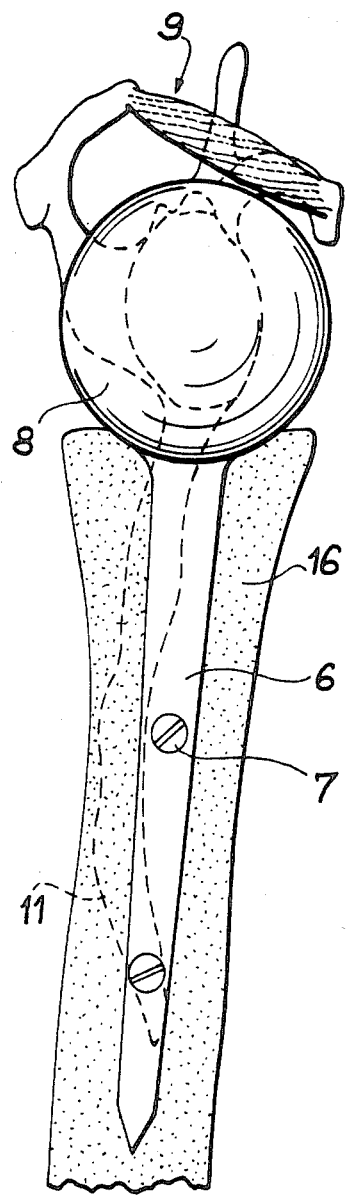
FIG. 7 an identical view of the humeral part of the prosthesis showing the humerus and the shoulder blade.

FIGS. 3a, 3b and 3c showing the different positions of the shoulder prosthesis according to the invention, when the arm is in the hanging position (FIG. 3a), semi-raised position (FIG. 3b) and completely raised position (FIG. 3c), illustrate that in all the positions of the arm, the non-dislocatable character of the prosthesis is simply due to gravity and/or the tractions exerted on the arm can only engage the cupula 5 on the sphere 4, without any risk of causing a dislocation in any position.

When the shoulder prosthesis according to the invention reaches the position of FIG. 3c, another important feature of the present invention is involved. Thus, the outer spherical part of cupula 5 is given a diameter close to that of a normal anatomical humeral head, so that in the raised position of the arm, said cupula can be housed beneath the acromioclavicular fornix 9. It is then the bones of said acromioclavicular fornix 9 which guarantee its stability at this time, insofar as a complementary raising stress or force relative to the arm takes place in the direction of arrow F in the drawing. As from this position, swivel joint is locked and, as in a normal shoulder, the possible complementary raising of the arm results from a total movement of the shoulder blade.

FIG. 3c shows another very important special feature of the invention. Rod 3 for fixing sphere 4 to shoulder